(12) United States Patent
Ho

(10) Patent No.: US 7,779,832 B1
(45) Date of Patent: *Aug. 24, 2010

(54) HEADGEAR FOR USE WITH A PATIENT INTERFACE DEVICE

(75) Inventor: Peter Ho, Pittsburgh, PA (US)

(73) Assignee: RIC Investments, LLC, Wilmington, DE (US)

( * ) Notice: Subject to any disclaimer, the term of this patent is extended or adjusted under 35 U.S.C. 154(b) by 364 days.

This patent is subject to a terminal disclaimer.

(21) Appl. No.: 10/622,562

(22) Filed: Jul. 18, 2003

Related U.S. Application Data

(60) Provisional application No. 60/402,336, filed on Aug. 9, 2002.

(51) Int. Cl.
| | |
|---|---|
| A62B 17/04 | (2006.01) |
| A62B 18/08 | (2006.01) |
| A61M 16/00 | (2006.01) |
| A61M 15/00 | (2006.01) |
| A41D 13/00 | (2006.01) |
| A61F 9/00 | (2006.01) |
| A61F 9/02 | (2006.01) |
| A42B 1/08 | (2006.01) |
| A42B 1/18 | (2006.01) |
| A63B 71/10 | (2006.01) |

(52) U.S. Cl. ............ 128/201.22; 128/206.13; 128/206.27; 128/207.17; 128/207.11; 128/204.11; 128/201.23; 2/9; 2/10; 2/424; 2/425; 2/452; 2/173

(58) Field of Classification Search ............ 128/201.22, 128/206.13, 206.27, 207.17, 207.11, 204.11, 128/201.23; 2/9, 10, 424, 425, 452, 173
See application file for complete search history.

(56) References Cited

U.S. PATENT DOCUMENTS

| | | | |
|---|---|---|---|
| 5,038,776 | A | 8/1991 | Harrison et al. |
| 5,441,046 | A | 8/1995 | Starr et al. |
| 5,517,986 | A | 5/1996 | Starr et al. |
| 5,542,128 | A * | 8/1996 | Lomas .................... 2/173 |
| 5,662,101 | A * | 9/1997 | Ogden et al. ........... 128/205.25 |
| 5,724,965 | A | 3/1998 | Handke et al. |
| 6,119,694 | A | 9/2000 | Correa et al. |
| 6,269,814 | B1 | 8/2001 | Blaszczykiewicz et al. |
| 6,422,238 | B1 | 7/2002 | Lithgow |
| 6,805,117 | B1 * | 10/2004 | Ho et al. ................. 128/201.22 |

FOREIGN PATENT DOCUMENTS

AU  9459430  2/1996

* cited by examiner

*Primary Examiner*—Loan H Thanh
*Assistant Examiner*—Nihir Patel
(74) *Attorney, Agent, or Firm*—Michael W. Haas

(57) ABSTRACT

A universal headgear is easy to use and creates an effective seal between a patient interface device, such as gas delivery mask, and a patient. The headgear of the present invention includes a halo-like headband formed from an elastomeric material. The headband includes contoured panels that allow the device to fit most people without circumference length adjustment. The halo headband is designed to maintain a substantially frusto-conical shape when worn. The present invention preferably includes an adjustable crossover strap on the top connecting the contoured panels that is adapted to hold the halo headband in position. The headpiece further includes connecting straps to adjustably connect the headgear to a patient interface device. The present headgear fits a wide range of head sizes and shapes, is easy to use, and provides increased stability.

36 Claims, 5 Drawing Sheets

HEADGEAR FOR USE WITH A PATIENT INTERFACE DEVICE

CROSS-REFERENCE TO RELATED APPLICATIONS

This application claims priority under 35 U.S.C. §119(e) from provisional U.S. patent application no. 60/402,336 filed Aug. 9, 2002, the contents of which are incorporated herein by reference.

BACKGROUND OF THE INVENTION

1. Field of the Invention

The present invention generally relates to a headgear, and, more particularly, to a headgear having a universal fit for a patient interface device, such as a gas delivery mask, and to a system for supplying a flow of gas to a patient that incorporates such a headgear.

2. Description of the Related Art

There are numerous situations where it is necessary or desirable to deliver a flow of breathing gas non-invasively to the airway of a patient, i.e., without intubating the patient or surgically inserting a tracheal tube in their esophagus. For example, it is known to ventilate a patient using a technique known as non-invasive ventilation. It is also known to deliver continuous positive airway pressure (CPAP) or variable airway pressure, which varies with the patient's respiratory cycle, to treat a medical disorder, such as sleep apnea syndrome, in particular, obstructive sleep apnea (OSA), or congestive heart failure.

Non-invasive ventilation and pressure support therapies involve the placement of a patient interface device, which is typically a nasal mask that covers the nose, a nasal/oral mask that covers the nose and mouth, or full face mask that covers the patient face, on the face of a patient. The patient interface device interfaces the ventilator or pressure support device with the airway of the patient, so that a flow of breathing gas can be delivered from the pressure/flow generating device to the airway of the patient. It is known to maintain such masks on the face of a wearer by a headgear having upper and lower straps, each having opposite ends threaded through connecting elements provided on the opposite sides and top of a mask. Because such masks are typically worn for an extended period of time, it is important the headgear maintain the mask in a tight enough seal against a patient's face without discomfort.

One such headgear is disclosed in U.S. Pat. No. 5,517,986 which is assigned to Respironics, Inc. of Pittsburgh, Pa., the assignee of the present application. The headgear of U.S. Pat. No. 5,517,986 which is incorporated by reference herein, includes a cap-like headpiece adapted to fit the crown and back of a patient's head. Lower straps provide a two-point connection with a gas delivery mask. Depending straps depending from the headpiece are connected to and moveable relative to the lower straps. Additionally, a pair of upper straps can be used to provide a four-point connection with the gas delivery mask if needed.

Another such headgear 10 manufactured by Respironics, Inc. is illustrated in FIG. 1. Headgear 10 comprises five straps 12, 14, 16, 18, 20 extending in a star-like manner from a rear joining piece 22, which is positionable along the rear portion of a patient's head. The three uppermost straps 12, 14, 16 are adapted to fit on the patient's head. Center top strap 12 extends from joining piece 22 across the top of the patient's head to the patient's forehead. Upper side straps 14, 16 on either side of top strap 12 extend from joining piece 22 along the sides of a patient's head above the ears to attach to top strap 12 at the patient's forehead. Top strap 12 includes a pair of elongated openings 24 through which upper side straps 14, 16 are threaded.

All of the straps include two components of a hook and loop fastener such as VELCRO. The exterior of the straps include a loop fastener portion, and a hook fastener tab portion 26 is attached to the end of each strap. When securing or fastening, the end of each upper side strap 14, 16 is bent back on itself to adhere hook fastener tab portion 26 to the exterior of the straps including the loop fastener portion. More specifically, hook fastener tab portion 26 of top strap 12 is adapted to be threaded through a connecting element of the gas delivery mask and then bent back on itself to adhere the hook fastener tab portion to the exterior loop fastener portion.

Lower connecting straps 18, 20 are adapted to be brought forward from rear joining piece 22 beneath the patient's ear and threaded through connecting elements on either side of the gas delivery mask. Tab portions 26 are bent back to adhere to the exterior loop fastener portion of lower connecting straps 18, 20.

Conventional headgear 10 provides a convenient three-point headgear yet lacks adjustability in the cross direction of the head. Further, headgear 10 lacks the ability to prevent top strap 12 from shifting on the patient's head in use. Therefore, a need exists for a headgear which is easy to use and adjust.

SUMMARY OF THE INVENTION

Accordingly, the present invention provides a universal headgear that creates an effective seal between a gas delivery mask and a patient and that overcomes the shortcomings of conventional headgear. The present invention further provides a headgear that is comfortable to the patient and fits a wide range of head sizes.

The headgear of the present invention includes a halo-like headband formed from an elastomeric material. The elastomeric headband having contoured panels allows the device to fit most people without circumference length adjustment. The halo headband is designed to maintain a substantially frusto-conical shape when worn. It rests and secures on the head at different positions with respect to the circumference length. The present invention preferably includes an adjustable crossover strap on the top connecting the contoured panels. The crossover strap is adapted to hold the halo headband in position. The crossover strap helps prevent the headband from falling out of position. This is most notable in patients with small head circumferences. Besides the three-point connecting strap adjustment, the crossover strap is the only other adjustment needed. The headpiece further includes connecting straps to adjustably connecting the headgear to a patient interface or gas delivery mask.

The present invention further comprises an assembly including a headgear and a gas delivery mask, and to a system for supplying a flow of gas to a patient that incorporates such a headgear. The headgear of the present invention fits a wide range of head sizes and shapes, is easy to use and provides increased stability.

These and other objects, features and characteristics of the present invention, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention.

DETAILED DESCRIPTION OF THE PRESENTLY PREFERRED EMBODIMENTS OF THE INVENTION

Figure 1:
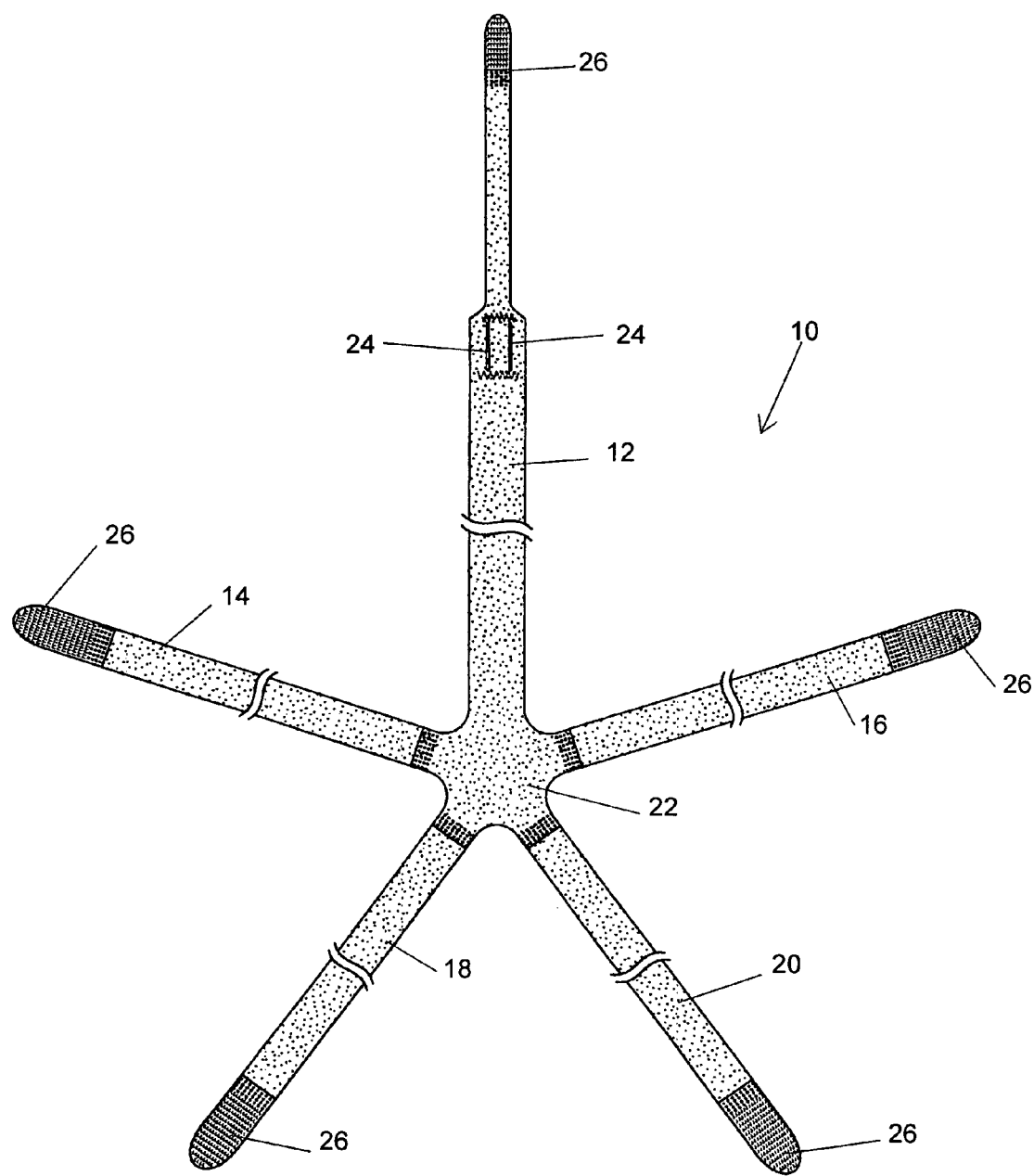
FIG. 1 is a plan view of the headgear according to the prior art.
Figure 2:
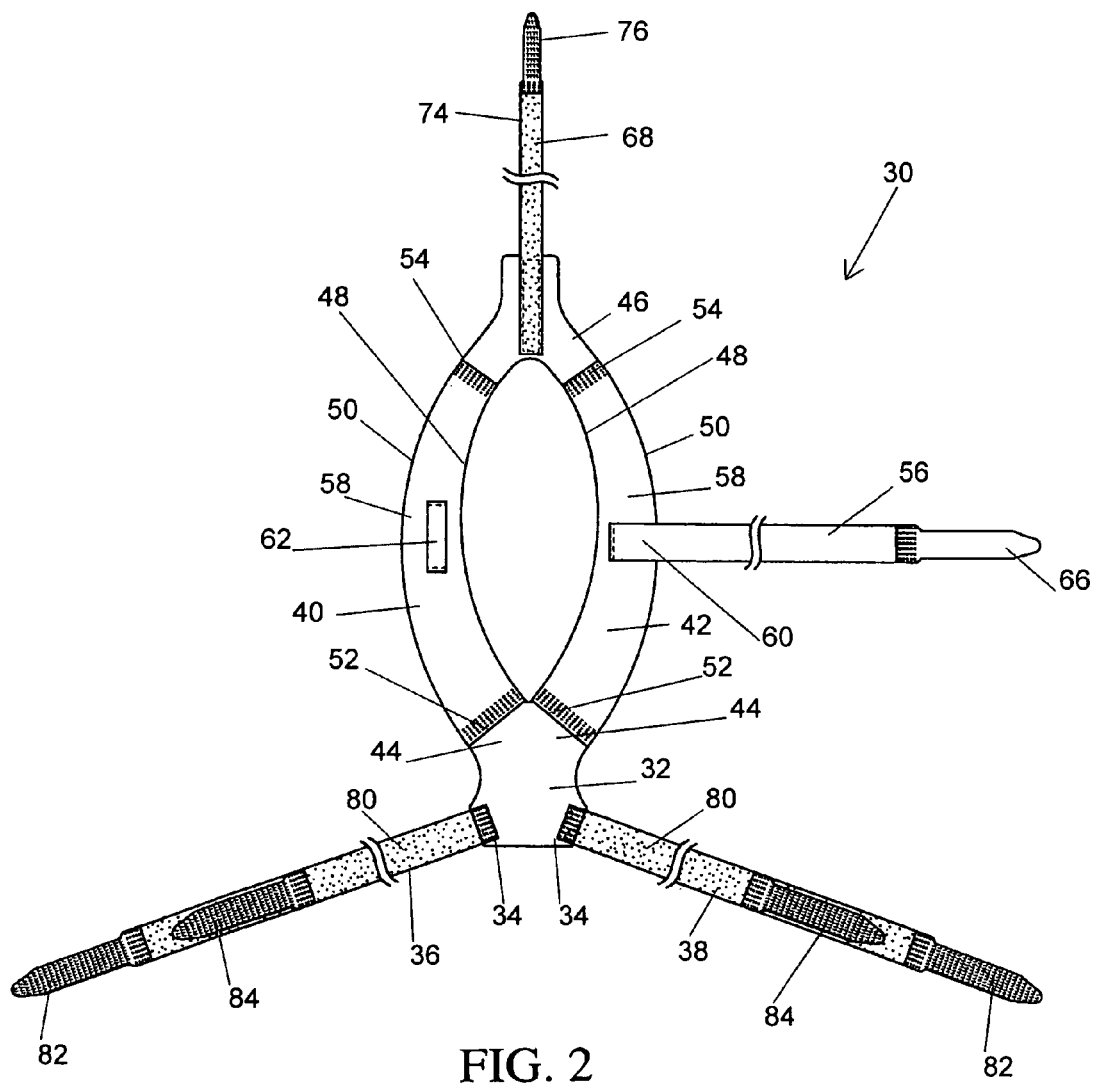
FIG. 2 is a plan view of the headgear according to the present invention.

FIGS. 2-5 illustrate an exemplary embodiment of a headgear 30 according to the principles to the present invention. Headgear 30 includes a rear joining piece 32 having lower corners 34 from which a pair of lower connecting straps 36, 38 extend. A pair of contoured panels 40, 42 extend from upper corners 44 of the joining piece. Contoured panels 40, 42 extend from rear joining piece 32, which is positionable along the rear of a patient's head to a Y-shaped front joining piece 46, which is positionable along the patient's forehead. In use, the contoured panels extend along the sides of the patient's head above the ears, as shown, for example, in FIGS. 3-5.

Contoured panels 40, 42 are crescent or arch-shaped having an upper edge 48 having a concave curvature and a lower edge 50 having a convex curvature. Each contoured panel 40, 42 further has a rear joining edge 52, which is connected to rear joining piece 32 and a front joining edge 54, which is connected to front joining piece 46. Rear joining edge 52 of each panel is preferably longer in length than front joining edge 54, so that each contoured panel 40, 42 generally tapers from its rear joining edge 52 to its front joining edge 54. Joining pieces 32 and 46 and contoured panels 40 and 42 are preferably stamped from material using a die cut process so that the resulting pieces are flat. However, when positioned on the head, the contoured panels and joining pieces form a substantially truncated conical or frusto-conical shaped headpiece. It is to be understood, however, that the present invention contemplates forming joining pieces 32 and 46 and contoured panels 40 and 42, or any combination thereof, as a single piece of material so that these pieces are integral with one another. An upper circumference following the upper edges 48 of the contoured panels 40, 42 is shorter in length than a lower circumference following the lower edges 50 of the contoured panels. The substantially frusto-conical shape and stretchiness of the headpiece allow the panels to fit a wide range of patients' heads.

Headgear 30 optionally, yet preferably, has an adjustable crossover strap 56 adapted to fit across the top of the patient's head from a middle portion 58 of one contoured panel to a middle portion 58 of the other contoured panel. The crossover strap 56 is attached at one end 60 to of one of the contoured panels, e.g., near upper edge 48. A loop 62 is attached to the other of the contoured panels. An exterior 64 (FIG. 5) of crossover strap 56 includes the loop fastener portion of a hook and loop fastener, such as VELCRO while an end tab portion 66 includes the hook portion. The end tab portion 66 (FIG. 4) is threaded through loop 62 and bent back on itself to adhere the hook portion to the loop portion.

The present invention contemplates other means of attaching and adjusting the crossover strap as well. In an exemplary embodiment, crossover strap 56 is formed from a stretchable material and loop 62 is formed from fabric. Optional crossover strap 56 provides adjustability in the cross direction of the head as well as stability by preventing downward displacement of the headgear 30.

The headgear 30 further includes an upper connecting strap 68 attached to the central portion of front joining piece 46. In use, upper connecting strap 68 depends downwardly from front joining piece 46 and across the patient's forehead (see FIGS. 3 and 4). Upper connecting strap 68 is adapted to be secured to a connecting element 70 disposed at the top of a patient interface device 72, such as a conventional gas delivery mask. Upper connecting strap 68 includes the components of a hook and loop type fastener such as VELCRO, for example, having the loop portion on an exterior 74 of upper connecting strap 68 and the hook portion on an end tab portion 76 at the end of upper connecting strap 68. End tab portion 76 of upper connecting strap 68 is threaded through connecting element 70 disposed on patient interface device 72 and then bent back on itself to adhere to the exterior loop portion 74 of upper connecting strap 68.

Figure 3:
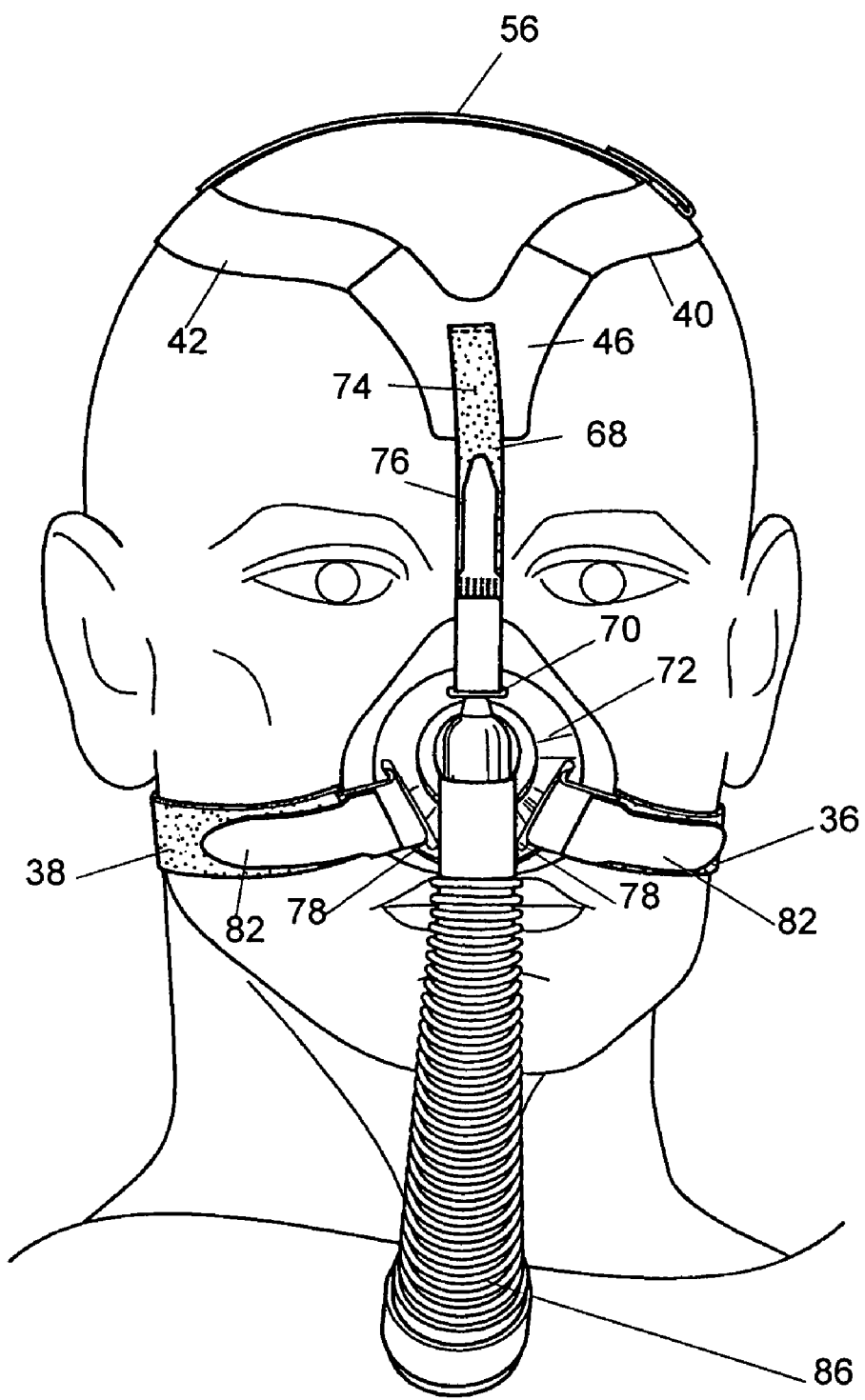
FIG. 3 is a front view of a patient wearing the headgear of FIG. 2 with a nasal mask.
Figure 4:
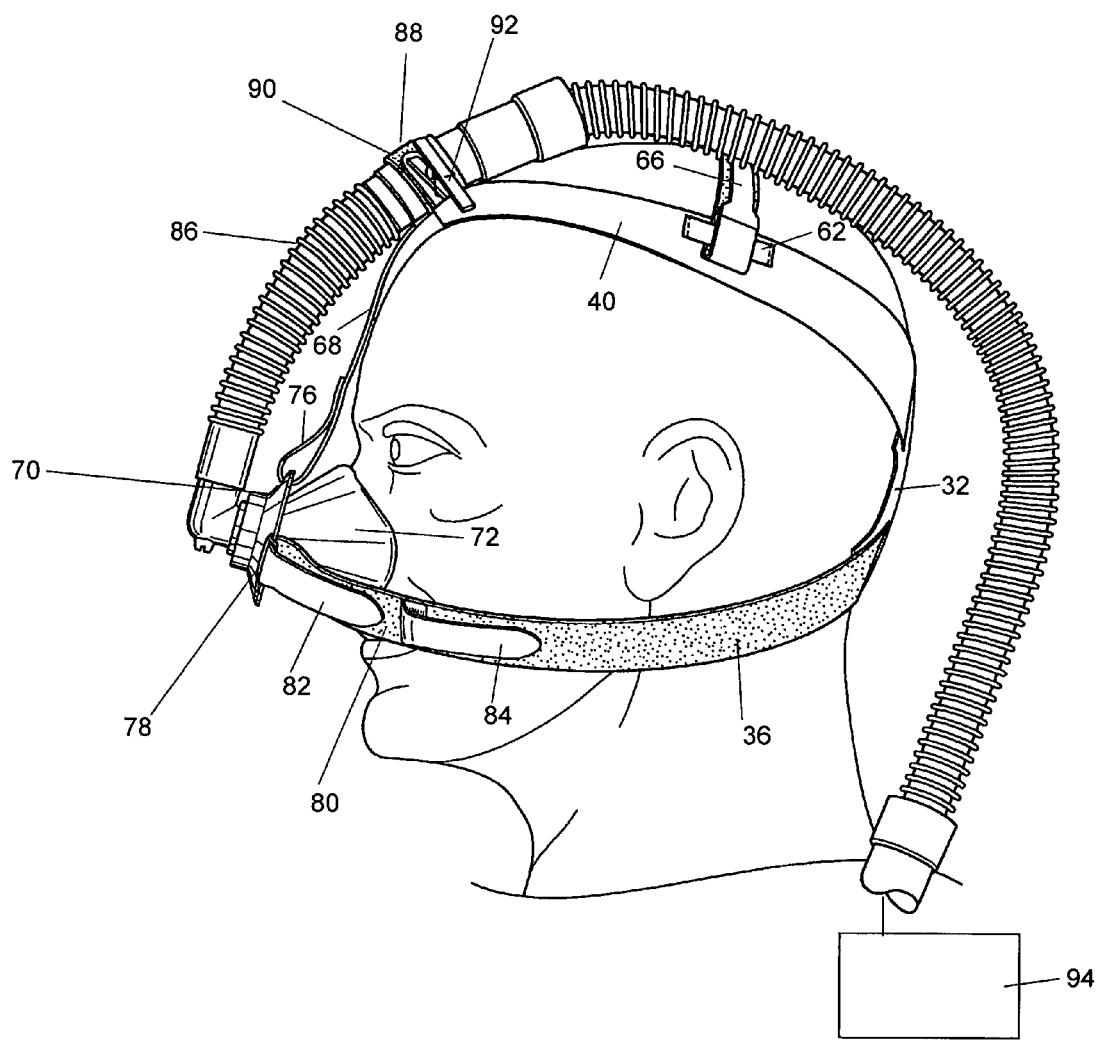
FIG. 4 is a side view of a patient wearing the headgear of FIG. 2.
Figure 5:
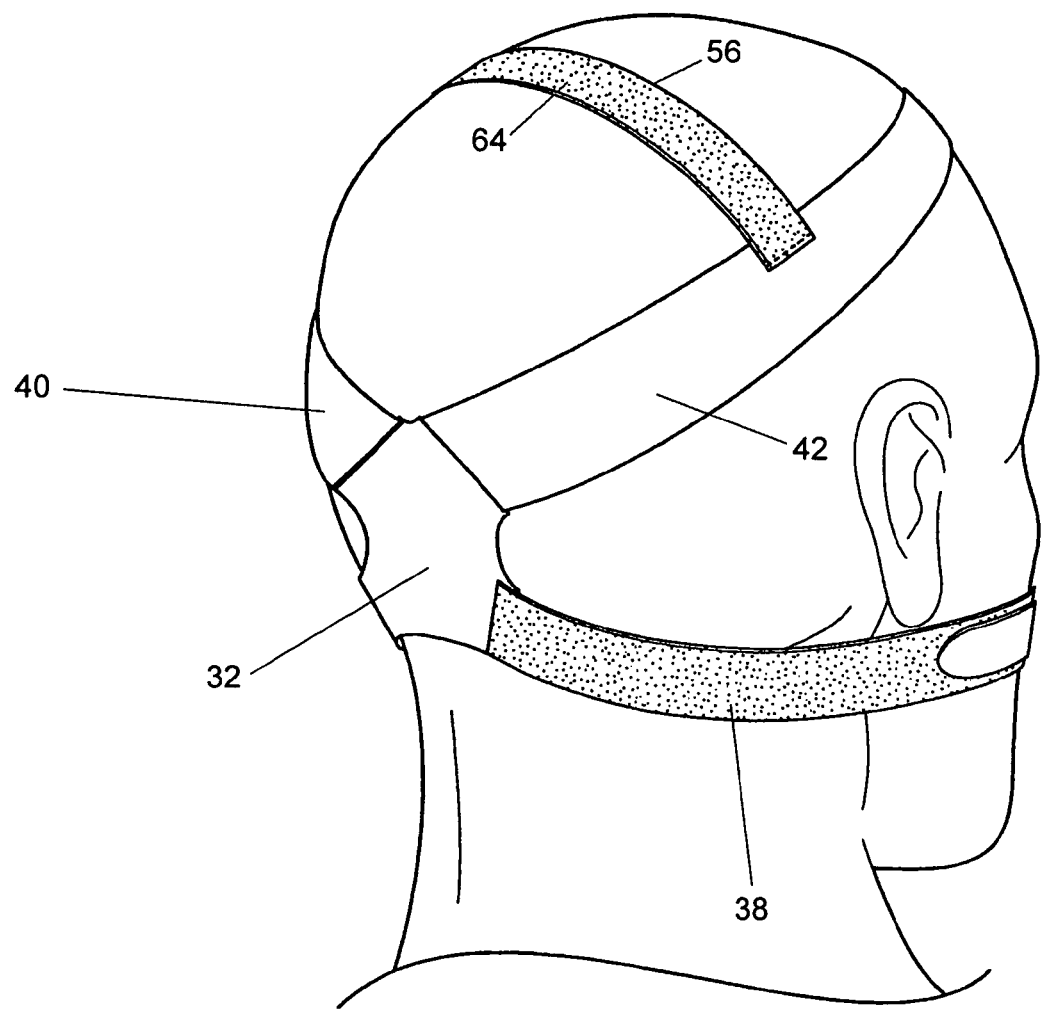
FIG. 5 is a rear perspective view of a patient wearing the headgear of FIG. 2.

The pair of lower connecting straps 36, 38 extend forwardly from the rear joining piece beneath the patient's ears and are adapted to be secured to connecting elements 78 disposed on the sides of patient interface device 72 (FIGS. 3 and 4). Like upper connecting strap 68, lower connecting straps 36, 38 preferably include two components of a hook and loop type fastener. For example, an exterior 80 of lower connecting straps 36, 38 includes a loop fastener portion and the hook fastener portion is disposed on an end tab portion 82 at the end of each lower connecting strap 36, 38. Thus, each lower connecting strap 36, 38 is adapted to be threaded through a connecting element 78 on the side of patient interface device 72 and then bent back on itself to adhere end tab portion 82 to exterior 80 of the lower connecting strap.

Preferably, but optionally, each lower connecting strap 36, 38 includes at least one intermediary tab portion 84 having a hook fastener portion. Each intermediary tab portion 84 is attached to exterior 80 of lower connecting straps 36, 38 between end tab portion 82 and the end of the strap attached to rear joining piece 32. When fitting the headgear 30 on a smaller size head, intermediary tab portion 84, as well the end tab portion 82, is threaded through connecting element 78 of patient interface device 72. Each intermediary tab portion is bent back on itself over connecting element 78 to secure the patient interface device to the headgear. Each end tab portion 82 is also secured to exterior 80 of lower connecting strap 36, 38.

The connecting straps 36, 38, 68 may be formed of an elastic material to provide for adjustment. Of course, the present invention contemplates the connecting straps 36, 38, 68 can use other forms of adjustment and connection other than hook and loop fasteners such as snaps or buckles. It should also be apparent that the other one of the hook and loop fastener component described above could be substituted for the component disclosed.

The contoured panels 40, 42 are preferably formed from a stretchy elastomeric material to allow for fitting various sized patients' heads. Preferably, the material is LYCRA laminated foam having sufficient elastic adjustability to adapt to different shaped heads as well as padding for comfort. Of course, the present invention contemplates the panels 40, 42 be made of other types of material such as NEOPRENE as long as the material provides sufficient elasticity and comfort as well as air permeability.

Similarly, the rear joining piece 32 and front joining piece 46 are preferably made of an elastic lightweight air permeable material such as LYCRA laminated foam. The present invention contemplates the joining pieces 32, 46 be made of other types of material such as NEOPRENE as long as it provides sufficient elasticity and comfort.

FIGS. 2-5 illustrates connection with a patient interface device 72 in the form of a nasal mask of the type disclosed in U.S. Pat. No. 6,412,488, the disclosure of which is incorporated by reference herein. However, the present invention may be used with other patient interface devices, including a nasal mask, a nasal/oral mask, and a full face mask. Also, the present invention contemplates modification of the front joining piece 46 to a T-shaped piece including two connecting straps for use with four point connecting masks.

In patient interface device 72 of the type shown in FIGS. 2-5, a conduit 86 that extends upwardly from the patient interface device and above the head of the patient. Note that in FIG. 3, the conduit is shown extending downwardly. While this configuration is contemplated by the present invention, it is considered desirable to anchor conduit 86 to headgear 30 for stability. To this end, a conduit stabilizer 88 is provided for stabilizing the conduit 86 relative to the headgear 30. See FIG. 4. This type of stabilizer 86 is also provided in the prior art headgear of FIG. 1 but not illustrated. Conduit stabilizer 88 comprises a loop of material 90 having a hook and loop type attachment, and an alligator type clip 92 attached to one end. Material 90 is looped around the conduit 86 and secured with the hook and loop type attachment while alligator type clip 92 is clipped to one of contoured panels 40, 42.

Patient interface device communicates a flow of breathing gas between the patient's airway and pressure generating device 94 (FIG. 4), such as a ventilator, CPAP device (FIG. 3), or variable pressure device, e.g., a BiPAP® device manufactured and distributed by Respironics, Inc., in which the pressure provided to the patient varies with the patient's respiratory cycle so that a higher pressure is delivered during inspiration than during expiration. Other variable pressure devices vary the pressure of gas delivered to the patient based on the detected condition of the patient, such as whether the patient is snoring, experiencing and apnea, hypopnea, etc.

Communicating a flow of breathing gas between the patient's airway and pressure generating device 94 includes delivering a flow of breathing gas to the patient from the pressure generating device 94 and exhausting a flow of gas from the patient to ambient atmosphere. The system for delivering a breathing gas to a patient according to the present invention comprises: 1) pressure or gas flow generating device 94 that produces a flow of gas; 2) conduit 86 having a first end portion operatively coupled to the gas flow generating device 94 and a second end portion, wherein the conduit carries the flow of gas from the gas flow generating device 94 during operation of the system; 3) patient interface device 72 assembly coupled to the second end portion of the conduit 86; and 4) headgear 30 as described above.

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims.

What is claimed is:
1. A headgear for a patient interface device comprising:
 (a) a headpiece, wherein the headpiece comprises:
  (1) contoured panels, each panel including an upper edge having a length and a lower edge having a length, the length of the upper edge is shorter than the length of the lower edge,
  (2) a rear joining piece positionable along a rear portion of a patient's head, and
  (3) a front joining piece positionable along a front portion of such a patient's head, wherein each of the contoured panels extend from the rear joining piece to the front joining piece;
 (b) a connecting strap attached to the headpiece and adapted for releasably connecting the headgear to the patient interface device; and
 (c) a crossover strap extending from one of the contoured panels and adapted to extend to another one of the contoured panels.

2. The headgear of claim 1, wherein the connecting strap is an upper connecting strap attached to the front joining piece and adapted to releasably connect the headgear to the patient interface device.

3. The headgear of claim 2, further comprising a lower connecting strap attached to the rear joining piece and adapted to releasably connect the headgear to the patient interface device.

4. The headgear of claim 3, wherein the upper and the lower connecting straps include hook and loop components for adjustably connecting the headgear to the patient interface device.

5. The headgear of claim 4, wherein the upper and lower connecting straps include a loop fastener portion on the exterior thereof and an end portion having a hook tab portion, wherein each hook tab portion is adapted for threading through a connecting element of the patient interface device and securing to the loop fastener portion.

6. The headgear of claim 1, wherein the crossover strap includes hook and loop components for adjustably connecting the crossover.

7. The headgear of claim 1, wherein each of the contoured panels has an arch-shape having an upper edge having a concave curvature and a lower edge having a convex curvature.

8. The headgear of claim 1, wherein the headpiece is formed from an elastomeric material.

9. The headgear of claim 1, further comprising a stabilizer attached to the headpiece and adapted to stabilize a conduit connected to the patient interface device.

10. A headgear and patient interface device comprising:
 1) a patient interface device adapted to fit over a portion of the face of a patient and having a connector element; and
 2) a headgear comprising:
  a) a headpiece; and
  b) a connecting strap attached to the headpiece and adapted to releasably connect the headgear to the connector element, wherein the headpiece comprises:
   (i) a plurality of contoured panels, each panel including an upper edge having a length, a lower edge having a length, an interior edge having a length, and an exterior edge having a length, wherein the interior edge is proximate to a top of a patient's head responsive to the headgear being worn by such a patient and the exterior edge is generally opposite the interior edge. wherein in each contoured panel the length of the upper edge is shorter than the length of the lower edge, wherein the interior edge is generally concave-shaped and the exterior edge is generally convex-shaped, and wherein contoured panels are arranged such that the interior edges of adjacent contoured panels face each other and are spaced apart from each other such that a gap is defined between the interior edges of adjacent contoured panels, (ii) a rear joining piece positionable along a rear portion of a patient's head, wherein the lower edge of each contoured panel is connected to the rear joining piece, and (iii) a front joining piece positionable along a front portion of such a patient's head, wherein the upper edge of each contoured panel is connected to the front joining piece, wherein the connecting strap extends from either the rear joining piece or the front joining piece.

11. The headgear and patient interface device of claim 10, wherein the connecting strap is an upper connecting strap attached to the front joining piece and adapted to releasably connect the headgear to the patient interface device.

12. The headgear and patient interface device of claim 11, further comprising a lower connecting strap attached to the rear joining piece and adapted to releasably connect the headgear to the patient interface device.

13. The headgear and patient interface device of claim 12, wherein the upper and the lower connecting straps include hook and loop components for adjustably connecting the headgear to the patient interface device.

14. The headgear and patient interface device of claim 13, wherein the upper and the lower connecting straps include a loop fastener portion on the exterior thereof and an end portion having a hook tab portion, and wherein each hook tab portion is threaded through the connecting element of the patient interface device and secured to the loop fastener portion.

15. The headgear and patient interface device of claim 10, wherein each of the first and the second contoured panels has an arch-shape having an upper edge having a concave curvature and a lower edge having a convex curvature.

16. The headgear and patient interface device of claim 10, further comprising a stabilizer attached to the headpiece and adapted to stabilize a conduit connected to the patient interface device.

17. The headgear and patient interface device of claim 10, wherein the patient interface device is a nasal mask, a nasal/oral mask, or a full face mask.

18. A headgear and patient interface device comprising:
1) a patient interface device adapted to fit over a portion of the face of a patient and having a connector element; and
2) a headgear comprising:
   a) a headpiece, wherein the headpiece comprises:
      (i) contoured panels, each panel including an upper edge having a length and a lower edge having a length, the length of the upper edge is shorter than the length of the lower edge;
      (ii) a rear joining piece positionable along a rear portion of a patient's head; and
      (iii) a front joining piece positionable along a front portion of such a patient's head, wherein each of the contoured panels extend from the rear joining piece to the front joining piece;
   b) a connecting strap attached to the headpiece and adapted to releasably connect the headgear to the connector element; and
   c) a crossover strap extending from one of the contoured panels and adapted to extend to another one of the contoured panels.

19. The headgear and patient interface device of claim 18, wherein the crossover strap includes hook and loop components for adjustably connecting the crossover strap.

20. A headgear and patient interface device comprising:
1) a patient interface device adapted to fit over a portion of the face of a patient and having a connector element; and
2) a headgear comprising:
   a) a headpiece formed from an elastomeric material, wherein the headpiece comprises:
      (i) contoured panels, each panel including an upper edge having a length, a lower edge having a length, an interior edge having a length, and an exterior edge having a length, wherein the interior edge is proximate to a top of a patient's head responsive to the headgear being worn by such a patient and the exterior edge is generally opposite the interior edge, wherein the length of the upper edge is shorter than the length of the lower edge, wherein the interior edge is generally concave-shaped and the exterior edge is generally convex-shaped, and wherein contoured panels are arranged such that the interior edges of adjacent contoured panels face each other and are spaced apart from each other such that a gap is defined between the interior edges of adjacent contoured panels;
      (ii) a rear joining piece positionable along a rear portion of a patient's head; and
      (iii) a front joining piece positionable along a front portion of such a patient's head, wherein each of the contoured panels extend from the rear joining piece to the front joining piece; and
   b) a connecting strap attached to the headpiece and adapted to releasably connect the headgear to the connector element.

21. A system for delivering a breathing gas to a patient comprising:
1) a gas flow generating device that produces a flow of gas;
2) a conduit having a first end portion operatively coupled to the gas flow generating device and a second end portion, wherein the conduit carries the flow of gas from the gas flow generating device during operation of the system;
3) a patient interface device coupled to the second end portion of the conduit, the patient interface device having a connector element; and
4) a headgear comprising:
   a) a headpiece; and
   b) a connecting strap attached to the headpiece and adapted to releasably connect the headgear to the connector element;
wherein the headpiece comprises:
   (i) a rear joining piece positionable along a rear portion of a patient's head;
   (ii) a front joining piece positionable along a front portion of such a patient's head; and
   (iii) a first contoured panel and a second contoured panel, wherein each of the first and the second contoured panels extend from the rear joining piece to the front joining piece, each of the first and second contoured panels including an upper edge having a length, a lower edge having a length, an interior edge having a length, and an exterior edge having a length, wherein the interior edge is proximate to a top of a patient's head responsive to the headgear being worn by such a patient and the exterior edge is generally opposite the interior edge, wherein in each of the first and second contoured panels the length of the upper edge is shorter than the length of the lower edge, wherein each lower edge is connected to the rear joining panel and each upper edge is connected to the front joining panel, wherein the connecting strap extends from either the rear joining piece or the front joining piece, wherein the interior edge is generally concave-shaped and the exterior edge is generally convex-shaped, and wherein contoured panels are arranged such that the interior edges of adjacent contoured panels face each other and are spaced apart from each other such that a gap is defined between the interior edges of adjacent contoured panels.

22. The system of claim 21, wherein the connecting strap is an upper connecting strap attached to the front joining piece adapted to releasably connect the headgear to the patient interface device.

23. The system of claim 22, further comprising a lower connecting strap attached to the rear joining piece and adapted to releasably connect the headgear to the patient interface device.

24. The system of claim 23, wherein the upper and the lower connecting straps include hook and loop components for adjustably connecting the headgear to the patient interface device.

25. The system of claim 24, wherein the upper and the lower connecting straps include a loop fastener portion on the exterior thereof and an end portion having a hook tab portion, and wherein each hook tab portion is threaded through the connecting element of the patient interface device and secured to the loop fastener portion.

26. The system of claim 21, further comprising a stabilizer attached to the headpiece and adapted to stabilize a conduit connected to the patient interface device.

27. The system of claim 21, wherein the patient interface device is a nasal mask, a nasal/oral mask, or a full face mask.

28. A system for delivering a breathing gas to a patient comprising:
1) a gas flow generating device that produces a flow of gas;
2) a conduit having a first end portion operatively coupled to the gas flow generating device and a second end portion, wherein the conduit carries the flow of gas from the gas flow generating device during operation of the system;
3) a patient interface device coupled to the second end portion of the conduit, the patient interface device having a connector element; and
4) a headgear comprising:
  a) a headpiece, wherein the headpiece comprises:
    (i) a rear joining piece positionable along a rear portion of a patient's head;
    (ii) a front joining piece positionable along a front portion of such a patient's head; and
    (iii) a first contoured panel and a second contoured panel, wherein each of the first and the second contoured panels extend from the rear joining piece to the front joining piece, each of the first and second contoured panels including an upper edge having a length and a lower edge having a length, wherein in each of the first and second contoured panels the length of the upper edge is shorter than the length of the lower edge;
  b) a connecting strap attached to the headpiece and adapted to releasably connect the headgear to the connector element; and
  c) a crossover strap extending from one of contoured panels and adapted to extend to another one of the contoured panels.

29. The system of claim 28, wherein the crossover strap includes hook and loop components for adjustably connecting the crossover strap.

30. A system for delivering a breathing gas to a patient comprising:
1) a gas flow generating device that produces a flow of gas;
2) a conduit having a first end portion operatively coupled to the gas flow generating device and a second end portion, wherein the conduit carries the flow of gas from the gas flow generating device during operation of the system;
3) a patient interface device coupled to the second end portion of the conduit, the patient interface device having a connector element; and
4) a headgear comprising:
  a) a headpiece formed form an elastomeric material, wherein the headpiece comprises:
    (i) a rear joining piece positionable along a rear portion of a patient's head;
    (ii) a front joining piece positionable along a front portion of such a patient's head; and
    (iii) a first contoured panel and a second contoured panel, wherein each of the first and the second contoured panels extend from the rear joining piece to the front joining piece, each of the first and second contoured panels including an upper edge having a length, a lower edge having a length, an interior edge having a length, and an exterior edge having a length, wherein the interior edge is proximate to a top of a patient's head responsive to the headgear being worn by such a patient and the exterior edge is generally opposite the interior edge, wherein in each of the first and second contoured panels the length of the upper edge is shorter than the length of the lower edge, wherein the interior edge is generally concave-shaped and the exterior edge is generally convex-shaped, and wherein contoured panels are arranged such that the interior edges of adjacent contoured panels face each other and are spaced apart from each other such that a gap is defined between the interior edges of adjacent contoured panels; and
  b) a connecting strap attached to the headpiece and adapted to releasably connect the headgear to the connector element.

31. A headgear for a patient interface device comprising:
(a) a headpiece having:
  (i) a substantially frusto-conical shape defined by a first contoured panel and a second contoured panel, wherein each of the first and the second contoured panels extend from the rear joining piece to the front joining piece,
  (ii) a rear joining piece positionable along a rear portion of a patient's head, and
  (iii) a front joining piece positionable along a front portion of such a patient's head;
(b) a connecting strap attached to the headpiece and adapted for releasably connecting the headgear to such a patient interface device; and (c) a crossover strap extending from one of the first or the second contoured panel and adapted to extend to a remaining other one of the first or the second contoured panel.

32. The headgear of claim 31, wherein the crossover strap includes hook and loop components for adjustably connecting the crossover strap to the first or the second contoured panel.

33. A headgear and patient interface device comprising:
1) a patient interface device adapted to fit over a portion of the face of a patient and having a connector element; and
2) a headgear comprising:
   a) a headpiece having:
      (i) a substantially frusto-conical shape defined by a first contoured panel and a second contoured panel,
      (ii) a rear joining piece positionable along a rear portion of a patient's head, and
      (iii) a front joining piece positionable along a front portion of such a patient's head, wherein each of the first and the second contoured panels extend from the rear joining piece to the front joining piece,
   b) a connecting strap attached to the headpiece and adapted to releasably connect the headgear to the connector element, and
   c) a crossover strap extending from one of the first or the second contoured panel and adapted to extend to a remaining other one of the first or the second contoured panel.

34. The headgear and patient interface device of claim 33, wherein the crossover strap includes hook and loop components for adjustably connecting the crossover strap to the first or the second contoured panel.

35. A system for delivering a breathing gas to a patient comprising:
1) a gas flow generating device that produces a flow of gas;
2) a conduit having a first end portion operatively coupled to the gas flow generating device and a second end portion, wherein the conduit carries the flow of gas from the gas flow generating device during operation of the system;
3) a patient interface device coupled to the second end portion of the conduit, the patient interface device having a connector element;
4) a headgear comprising:
   a) a headpiece having (i) a substantially frusto-conical shape defined by a first contoured panel and a second contoured panel, (ii) a rear joining piece positionable along a rear portion of a patient's head, and (iii) a front joining piece positionable along a front portion of such a patient's head, wherein each of the first and the second contoured panels extend from the rear joining piece to the front joining piece;
   b) a connecting strap attached to the headpiece and adapted to releasably connect the headgear to the connector element; and
   c) a crossover strap extending from one of the first or the second contoured panel and adapted to extend to a remaining other one of the first or the second contoured panel.

36. The system of claim 35, wherein the crossover strap includes hook and loop components for adjustably connecting the crossover strap to the first or the second contoured panel.

\* \* \* \* \*